US009676944B2

(12) United States Patent
Wai et al.

(10) Patent No.: US 9,676,944 B2
(45) Date of Patent: *Jun. 13, 2017

(54) METHODS OF INCREASING THE SOLUBILITY OF MATERIALS IN SUPERCRITICAL CARBON DIOXIDE

(71) Applicants: Micron Technology, Inc., Boise, ID (US); University of Idaho, Moscow, ID (US)

(72) Inventors: Chien M. Wai, Moscow, ID (US); Hiroyuki Ohde, Higashi-Hiroshima (JP); Stephen J. Kramer, Boise, ID (US)

(73) Assignees: Micron Technology, Inc., Boise, ID (US); Idaho Research Foundation, Moscow, ID (US)

( * ) Notice: Subject to any disclaimer, the term of this patent is extended or adjusted under 35 U.S.C. 154(b) by 101 days.

This patent is subject to a terminal disclaimer.

(21) Appl. No.: 14/571,525

(22) Filed: Dec. 16, 2014

(65) Prior Publication Data
US 2015/0096468 A1     Apr. 9, 2015

Related U.S. Application Data

(62) Division of application No. 13/544,532, filed on Jul. 9, 2012, now Pat. No. 8,912,238, which is a division
(Continued)

(51) Int. Cl.
*C09D 1/00* (2006.01)
*C23C 18/00* (2006.01)
(Continued)

(52) U.S. Cl.
CPC ............... *C09D 1/00* (2013.01); *C23C 16/22* (2013.01); *C23C 18/00* (2013.01); *C23C 18/122* (2013.01);
(Continued)

(58) Field of Classification Search
CPC ............ Y02P 20/544; H01L 21/02101; B01D 11/0203; B01D 11/0407; B01D 15/40
See application file for complete search history.

(56) References Cited

U.S. PATENT DOCUMENTS 4,707,174 A     11/1987   Johnson et al.
H0626 H          4/1989   Covino
(Continued)

FOREIGN PATENT DOCUMENTS

DE      10048654 A1     4/2002
JP     2002303694 A    10/2002
WO      9203378 A1      3/1992

OTHER PUBLICATIONS

Bocquet et al., "A new TiO2 film deposition process in a supercritical fluid", Surface and Coatings Technology, 1994, vol. 70, pp. 73-78.
(Continued)

*Primary Examiner* — Michael A Salvitti
(74) *Attorney, Agent, or Firm* — TraskBritt

(57) ABSTRACT

Methods of increasing the solubility of a base in supercritical carbon dioxide include forming a complex of a Lewis acid and the base, and dissolving the complex in supercritical carbon dioxide. The Lewis acid is soluble in supercritical carbon dioxide, and the base is substantially insoluble in supercritical carbon dioxide. Methods for increasing the solubility of water in supercritical carbon dioxide include dissolving an acid or a base in supercritical carbon dioxide to form a solution and dissolving water in the solution. The acid or the base is formulated to interact with water to solubilize the water in the supercritical carbon dioxide. Some compositions include supercritical carbon dioxide, a hydrolysable metallic compound, and at least one of an acid
(Continued)

Top

X-section and a base. Some compositions include an alkoxide and at least one of an acid and a base.

20 Claims, 1 Drawing Sheet

Related U.S. Application Data of application No. 11/075,771, filed on Mar. 9, 2005, now Pat. No. 8,241,708.

(51) Int. Cl.
<table>
<tr><td>C23C 18/12</td><td>(2006.01)</td></tr>
<tr><td>H01L 21/316</td><td>(2006.01)</td></tr>
<tr><td>C23C 16/22</td><td>(2006.01)</td></tr>
<tr><td>B01D 11/04</td><td>(2006.01)</td></tr>
<tr><td>B01D 11/02</td><td>(2006.01)</td></tr>
<tr><td>H01L 21/02</td><td>(2006.01)</td></tr>
<tr><td>B01D 15/40</td><td>(2006.01)</td></tr>
</table>

(52) U.S. Cl.
CPC ........ *C23C 18/1208* (2013.01); *H01L 21/316* (2013.01); *B01D 11/0203* (2013.01); *B01D 11/0407* (2013.01); *B01D 15/40* (2013.01); *H01L 21/02101* (2013.01); *Y02P 20/544* (2015.11)

(56) References Cited

U.S. PATENT DOCUMENTS

<table>
<tr><td>4,970,093 A</td><td></td><td>11/1990</td><td>Sievers et al.</td></tr>
<tr><td>5,275,796 A</td><td></td><td>1/1994</td><td>Tillotson et al.</td></tr>
<tr><td>5,314,724 A</td><td></td><td>5/1994</td><td>Tsukune et al.</td></tr>
<tr><td>5,354,715 A</td><td></td><td>10/1994</td><td>Wang et al.</td></tr>
<tr><td>5,395,805 A</td><td></td><td>3/1995</td><td>Droege et al.</td></tr>
<tr><td>5,525,643 A</td><td></td><td>6/1996</td><td>Macip-Boulis et al.</td></tr>
<tr><td>5,589,105 A</td><td></td><td>12/1996</td><td>DeSimone et al.</td></tr>
<tr><td>5,649,278 A</td><td></td><td>7/1997</td><td>Dunmead</td></tr>
<tr><td>5,730,874 A</td><td>*</td><td>3/1998</td><td>Wai .................. B01D 11/0203 134/1</td></tr>
<tr><td>5,770,085 A</td><td>*</td><td>6/1998</td><td>Wai .................. B01D 11/0203 210/638</td></tr>
<tr><td>5,789,027 A</td><td></td><td>8/1998</td><td>Watkins et al.</td></tr>
<tr><td>5,840,193 A</td><td>*</td><td>11/1998</td><td>Smart .................. C22B 3/0005 210/601</td></tr>
<tr><td>5,872,257 A</td><td>*</td><td>2/1999</td><td>Beckman ............... B82Y 30/00 210/634</td></tr>
<tr><td>5,965,025 A</td><td>*</td><td>10/1999</td><td>Wai .................. B01D 11/0203 210/634</td></tr>
<tr><td>6,090,675 A</td><td></td><td>7/2000</td><td>Lee et al.</td></tr>
<tr><td>6,132,491 A</td><td>*</td><td>10/2000</td><td>Wai .......................... B22F 9/24 210/757</td></tr>
<tr><td>6,187,911 B1</td><td>*</td><td>2/2001</td><td>Wai ....................... C22B 3/0005 210/634</td></tr>
<tr><td>6,541,278 B2</td><td></td><td>4/2003</td><td>Morita et al.</td></tr>
<tr><td>6,596,388 B1</td><td></td><td>7/2003</td><td>Obeng et al.</td></tr>
<tr><td>6,689,700 B1</td><td></td><td>2/2004</td><td>Watkins et al.</td></tr>
<tr><td>6,699,797 B1</td><td></td><td>3/2004</td><td>Morris et al.</td></tr>
<tr><td>6,716,663 B2</td><td></td><td>4/2004</td><td>Morita et al.</td></tr>
<tr><td>6,864,156 B1</td><td></td><td>3/2005</td><td>Conn</td></tr>
<tr><td>6,953,041 B2</td><td></td><td>10/2005</td><td>DeYoung et al.</td></tr>
<tr><td>8,241,708 B2</td><td></td><td>8/2012</td><td>Wai et al.</td></tr>
<tr><td>2002/0167254 A1</td><td></td><td>11/2002</td><td>Craig et al.</td></tr>
<tr><td>2003/0129618 A1</td><td></td><td>7/2003</td><td>Moronne et al.</td></tr>
<tr><td>2003/0157248 A1</td><td></td><td>8/2003</td><td>Watkins et al.</td></tr>
<tr><td>2003/0183043 A1</td><td></td><td>10/2003</td><td>Wai et al.</td></tr>
<tr><td>2003/0186110 A1</td><td></td><td>10/2003</td><td>Sloop</td></tr>
<tr><td>2004/0003828 A1</td><td></td><td>1/2004</td><td>Jackson</td></tr>
<tr><td>2004/0023453 A1</td><td></td><td>2/2004</td><td>Xu et al.</td></tr>
<tr><td>2004/0063300 A1</td><td></td><td>4/2004</td><td>Chi</td></tr>
<tr><td>2004/0071873 A1</td><td></td><td>4/2004</td><td>DeYoung et al.</td></tr>
<tr><td>2004/0118812 A1</td><td></td><td>6/2004</td><td>Watkins et al.</td></tr>
<tr><td>2005/0029490 A1</td><td></td><td>2/2005</td><td>Subawalla et al.</td></tr>
<tr><td>2005/0186515 A1</td><td></td><td>8/2005</td><td>Watkins</td></tr>
<tr><td>2006/0194928 A1</td><td></td><td>8/2006</td><td>Charpentier et al.</td></tr>
<tr><td>2006/0204651 A1</td><td>*</td><td>9/2006</td><td>Wai ......................... C23C 18/00 427/97.7</td></tr>
<tr><td>2015/0315540 A1</td><td>*</td><td>11/2015</td><td>Matthews ............ C12N 5/0081 435/378</td></tr>
</table>

OTHER PUBLICATIONS

Hong et al, "Photocatalytic decomposition of p-nitrophenol over titanium dioxides prepared in water-in-carbon dioxide microemulsion", Catalysis Today, vols. 93-95, Sep. 1, 2004, (published online Jul. 28, 2004), pp. 871-876.

Loy et al, "Direct Formation of Aerogels by Sol-Gel Polymerizations of Alkoxysilanes in Supercritical Carbon Dioxide", JACS, Nov. 18, 1997, vol. 9, Issue 11, pp. 2264-2268.

Tadros et al, "Synthesis of titanium dioxide particles in supercritical C02", The Journal of Supercritical Fluids, Sep. 1996, vol. 9, Issue 3, pp. 172-176.

Woods et al., Materials processing in supercritical carbon dioxide: surfactants, polymers and biomaterials, J. Mater. Chem., vol. 14, No. 11, pp. 1663-1678 (2004).

Ye et al, "Immersion Deposition of Metal Films on Silicon and Germanium Substrates in Supercritical Carbon Dioxide", Chem. Mater., 2003, (published online Nov. 16, 2002), vol. 15, Issue 1, pp. 83-91.

\* cited by examiner

SEM micrographs
Plane Si wafer
*Top*     FIG. 1A
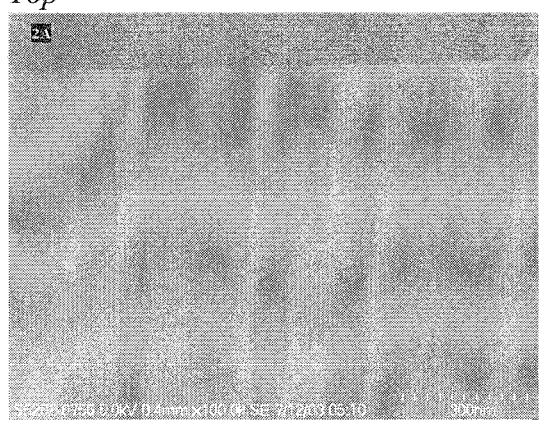
*X-section*     FIG. 1B
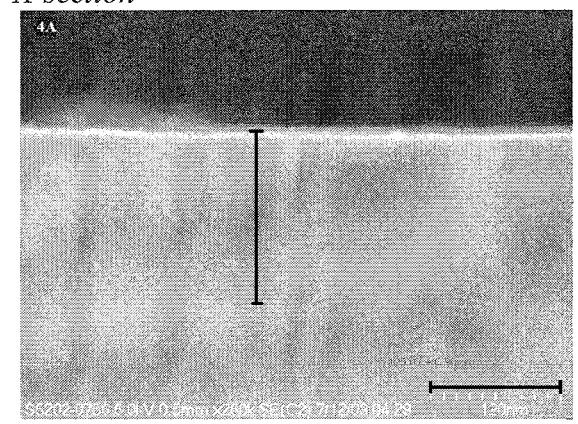
Si wafer with fine structures
*X-section*     FIG. 1C
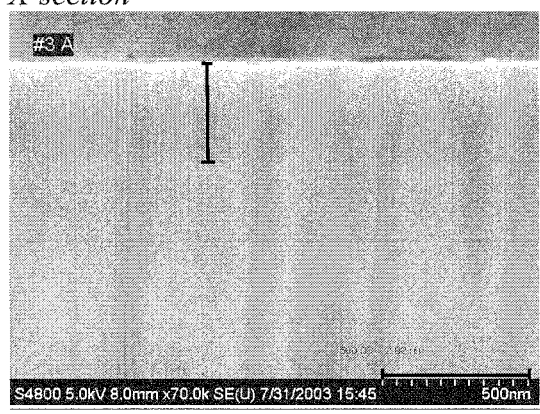
FIG 1D
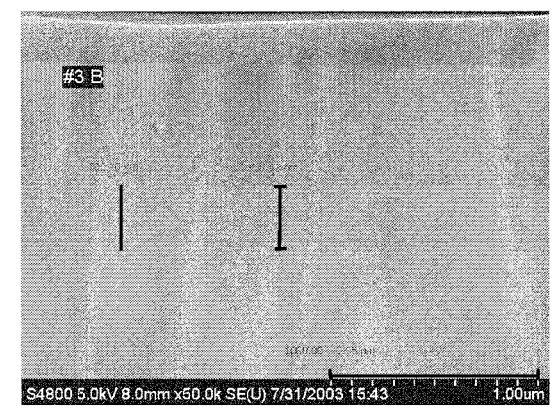

METHODS OF INCREASING THE SOLUBILITY OF MATERIALS IN SUPERCRITICAL CARBON DIOXIDE

CROSS-REFERENCE TO RELATED APPLICATIONS

This application is a divisional of U.S. patent application Ser. No. 13/544,532, filed Jul. 9, 2012, now U.S. Pat. No. 8,912,238, issued Dec. 16 2014, which is a divisional of U.S. patent application Ser. No. 11/075,771, filed Mar. 9, 2005, now U.S. Pat. No. 8,241,708, issued Aug. 14, 2012, the disclosure of each of which is hereby incorporated herein in its entirety by this reference.

BACKGROUND

Insulator oxide films, particularly silicon oxide films, have conventionally been made by methods such as thermal oxidation of silicon, physical vapor deposition and chemical vapor deposition, most typically chemical vapor deposition. However, chemical vapor deposition requires high temperatures, e.g., above 300° C., even with the aid of a plasma. Newer, lower temperature techniques, known as Chemical Fluid Deposition (CFD), are based on chemical deposition of the oxide films from a supercritical fluid solution have been developed.

U.S. Pat. No. 4,970,093 describes a method for depositing a film of a desired material on a substrate comprising dissolving at least one reagent in a supercritical fluid comprising at least one solvent. Either the reagent is capable of reacting with, or is a precursor of, a compound capable of reacting with the solvent to form the desired product, or at least one additional reagent is included in the supercritical solution and is capable of reacting with, or is a precursor of, a compound capable of reacting with the first reagent or with a compound derived from the first reagent to form the desired material. The supercritical solution is expanded to produce a vapor or aerosol and a chemical reaction is induced in the vapor or aerosol so that a film of the desired material resulting from the chemical reaction is deposited on the substrate surface. In an alternate embodiment, the supercritical solution containing at least one reagent is expanded to produce a vapor or aerosol which is then mixed with a gas containing at least one additional reagent. A chemical reaction is induced in the resulting mixture so that a film of the desired material is deposited.

U.S. Pat. No. 5,789,027 describes methods for depositing a film of material on the surface of a substrate by i) dissolving a precursor of the material into a supercritical or near-supercritical solvent to form a supercritical or near-supercritical solution; ii) exposing the substrate to the solution, under conditions at which the precursor is stable in the solution; and iii) mixing a reaction reagent into the solution under conditions that initiate a chemical reaction involving the precursor, thereby depositing the material onto the solid substrate, while maintaining supercritical or near-supercritical conditions. The invention also includes similar methods for depositing material particles into porous solids, and films of materials on substrates or porous solids having material particles deposited in them.

U.S. Pat. No. 6,541,278 describes a semiconductor substrate that is placed within a housing. By supplying organometallic complexes and carbon dioxide in a supercritical state into the housing, a BST thin film is formed on a platinum thin film, while at the same time, carbon compounds, which are produced when the BST thin film is formed are removed. The solubility of carbon compounds in the supercritical carbon dioxide is very high, and yet the viscosity of the supercritical carbon dioxide is low. Accordingly, the carbon compounds are removable efficiently from the BST thin film. An oxide or nitride film may also be formed by performing oxidation or nitriding at a low temperature using water in a supercritical or subcritical state, for example.

U.S. Pat. No. 6,716,663 describes a method wherein a semiconductor substrate is placed within a housing. By supplying organometallic complexes and carbon dioxide in a supercritical state into the housing, a BST thin film is formed on a platinum thin film, while at the same time, carbon compounds, which are produced when the BST thin film is formed, are removed. The solubility of carbon compounds in the supercritical carbon dioxide is very high, and yet the viscosity of the supercritical carbon dioxide is low. Accordingly, the carbon compounds are removable efficiently from the BST thin film. An oxide or nitride film may also be formed by performing oxidation or nitriding at a low temperature using water in a supercritical or subcritical state, for example.

Although these methods of chemical deposition form supercritical fluid solutions provide advantages over conventional deposition techniques, they can still be improved. In particular, faster reaction/deposition rates are desired. Also, providing a broader array of precursors and reagents would also be advantageous.

BRIEF SUMMARY OF THE INVENTION

A hallmark of the present invention is the rapid deposition of oxide formations via acid or base catalyzed CFD processes.

In one embodiment, the invention is a method for forming an insulating structure, the method comprising hydrolyzing an alkoxide in a supercritical fluid in the presence of an acid catalyst or a base catalyst such that an insulating oxide material is deposited from the supercritical fluid to form the insulating structure.

Another embodiment of the invention is a composition comprising a solution of an alkoxide and either an acid or a base in supercritical carbon dioxide.

A further embodiment of the invention is a method of forming a material having a high dielectric content, the method comprising the steps of forming a solution of a hydrolysable alkoxide and a catalyst, the catalyst comprising an acid or a base, in supercritical carbon dioxide; and, reacting the hydrolysable alkoxide with water to deposit an oxide having a dielectric constant at least about 10.

Another embodiment of the invention is a method of producing an insulating film, the method comprising forming a solution of a hydrolysable alkoxide and a catalyst, the catalyst comprising an acid or a base, in supercritical carbon dioxide; contacting a substrate with the supercritical carbon dioxide solution; and, reacting the hydrolysable alkoxide with water to deposit a film of an oxide having a dielectric constant at least equal to silicon dioxide.

Yet another embodiment is a method for producing fine structures of an insulating material, the method comprising forming a solution of a hydrolysable alkoxide and a catalyst, the catalyst comprising an acid or a base, in supercritical carbon dioxide; contacting a substrate with the supercritical carbon dioxide solution, wherein the substrate comprises structures having high aspect ratios of at least 5; and, reacting the hydrolysable alkoxide with water to deposit an oxide having a dielectric constant at least equal to silicon dioxide, wherein the oxide fills the high aspect ratio structures.

In a further embodiment, the invention is a method of increasing the solubility of acids in supercritical carbon dioxide, the method comprising combining supercritical carbon dioxide, a Lewis base that is soluble in supercritical carbon dioxide, and an acid that is substantially insoluble in supercritical carbon dioxide such that the Lewis base and the acid form a complex that is soluble in supercritical carbon dioxide.

Another embodiment is a method of increasing the solubility of bases in supercritical carbon dioxide, the method comprising combining supercritical carbon dioxide, a Lewis acid that is soluble in supercritical carbon dioxide, and a base that is substantially insoluble in supercritical carbon dioxide such that the Lewis acid and the base form a complex that is soluble in supercritical carbon dioxide.

Yet another embodiment is a method for increasing the solubility of water in supercritical carbon dioxide, the method comprising combining supercritical carbon dioxide with an acid or base, wherein the acid or base is soluble, or solubilizable, in supercritical carbon dioxide and the acid or base interacts with water to solubilize the water in the supercritical carbon dioxide.

Still yet another embodiment is a method of forming a material having a low dielectric content, the method comprising the steps of forming a solution of a hydrolysable alkoxide and a catalyst, the catalyst comprising an acid or a base, in supercritical carbon dioxide, and reacting the hydrolysable alkoxide with water to deposit an oxide having a dielectric constant less than about 3.

Various other features, objects and advantages of the present invention will be made apparent from the following detailed description and the drawings.

BRIEF DESCRIPTION OF THE DRAWINGS

In the following detailed description, references made to the accompanying drawings that form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the spirit and scope of the present invention.

FIGS. 1A-1D show SEM images of a silicon dioxide film formed by a method of this invention.

DETAILED DESCRIPTION OF THE INVENTION

This invention is an improved method of conducting chemical reactions in supercritical, or near supercritical, carbon dioxide (SCD). In one preferred embodiment, the invention is a method for producing metal or semi-metal oxide deposits by hydrolysis of at least one hydrolysable precursor in supercritical carbon dioxide (SCD). Specifically, the hydrolysis reaction can be catalyzed by the presence of either an acid or a base.

The hydrolysable precursor is a typically a hydrolysable metallic compound. As used herein, the terms "metal" and "metallic" are to be construed broadly to encompass metals, the semi-metals (also known as metalloids) and phosphorus. The semi-metals are typically considered to be boron, silicon, germanium, arsenic, antimony, tellurium, and polonium.

The hydrolysable metallic compound precursor must be soluble or partially soluble in supercritical carbon dioxide (SCD). Unlike a normal fluid solvent, SCD has virtually no surface tension. As such, SCD is freely miscible with all gases because of the mutual lack of surface tension. Therefore, the terms "solubility" and "soluble" are used in the broadest sense to mean the ability or tendency of one substance to blend uniformly with another and the term "solution" is used to designate both true solutions (i.e., solids dissolved in a solvent) and uniform mixtures of miscible fluids. The SCD may include one or more co-solvents such as an alcohol (e.g., methanol, ethanol, etc.) or other semi-polar solvent (e.g., acetone) added to further aid in dissolution of the metal alkoxide, metal complex or salt. Additionally, this method could be applicable to reverse micelle structures that contain a $CO_2$ immiscible solvent that is the carrier for one or more of the reactants. Some typical surfactants for a reverse micelle in SCD are bis-(2-ethylhexyl)sulfosuccinate (AOT), Zonyl FSJ (contains one or more fluoroalkylphosphate ester salt), and poly(1,1,-dihydroperfluoro octyl acrylate)-b-poly (ethylene oxide) and others in review article: Helen M. Woods, Marta M. C. G. Silva, Cécile Nouvel, Kenin M. Shakesheff and Stven M. Howdle, Materials processing in supercritical carbon dioxide: surfactants, polymers and biomaterials, J. Mater. Chem., 2004, 14 (11), 1663-1678.

Generally, the hydrolysable metallic compounds known from the field of Sol-Gel chemistry should be appropriate for use in this inventive method under the right processing conditions. Examples of such compounds are:

1) Metal alkoxide with the structure M(OR), such as ethoxides (OEt), propoxides (OPr), butoxides (OBu), etc., and associated oligomers species $[M(OR)_n]_m$, where M is at least one metal atom, R is any alkyl group and may be the same or different each occurrence, and m and n are constants that are determined as needed to balance the electronic charge. Preferably, M is at least one of silicon, boron, hafnium, aluminum, phosphorus, zirconium, titanium, barium, lanthanum, or yttrium. Typically, R is a methyl, ethyl, propyl, or butyl group. A non-limiting list of suitable metallic alkoxides includes silicon tetra alkoxy compounds (such as tetraethyl orthosilicate (TEOS), tetramethoxysilane (TMOS), tetrapropoxysilane (TPOS), and tetrabutyloxysilane (TBOS)), hafnium tert-butoxide, aluminum ethoxide and aluminum isopropoxide. These and other metallic alkoxides are commercially available, such as from Gelest, Inc. More than one metallic alkoxide precursor may be used when a complex oxide, e.g., BST, is to be deposited. M-O-M linkages can exist in these materials, as well. Included are reaction products of metal alkoxides with organic hydroxy compounds such as alcohols, silanols $R_3SiOH$, glycols $OH(CH_2)_nOH$, carboxylic and hydroxycarboxylic acids, hydroxyl surfactants etc.

2) Metal carboxylates $M(O_2COR)_n$, and carboxylate oligomers and polymers $[M(O_2CR)_n]_m$, as well as hydrates thereof, where M is at least one metal atom, R is any alkyl group and may be the same or different each occurrence, and m (m stands for the degree of association or molecular complexity or nuclearity) and n are constants that are determined as needed to balance the electronic charge.

3) Metal β-diketonates $[M(RCOCHCOR')_n]$ and oligomeric and polymeric materials $[M(RCOCHCOR')_n]$, as well as adducts $M(\beta\text{-diketonates})_nL_x$ where M is at least one metal atom, R and Ŕ are any alkyl group and may be the same or different each occurrence, n is a constant determined as needed to balance the electronic charge, and L usually has a nitrogen or oxygen donor sites such as water, alcohols, ethers, amines, etc.

4) Metal alkoxide derived heteroleptic species (i.e., species with different types of ligands) such as $M(OR)_{n-x}Z_x$ (Z=β-diketonates or $O_2CR$), where M is at least one metal atom, R is any alkyl group and may be the same or different each occurrence, and m and x are constants that are determined as needed to balance the electronic charge.

5) ORganically MOdified SILanes (ORMOSILS) of general formula $(RO)_{4-x}SiZ_x$ where R is any alkyl group, Z is another functional (e.g., acrylate, epoxide, vinyl, etc.) or non-functional alkyl group forming a stable Si—C bond, and x is a constant chosen to balance electronic charge.

6) Heterometallic precursors ($M_xM_y'$, $M,My'M_z''$) with such forms as, but not limited to $M_xM'_y(OR)_n$, where M, M' and M'' are different metal atoms, R is any alkyl group and may be the same or different each occurrence, and n, x, y, and z are constants that are determined as needed to balance the electronic charge.

7) Metal salts, halides $MX_n$, chlorates, hypochlorites, nitrates, nitrites, phosphates, phosphites, sulfates, sulfites, etc., where M is a metal atom, X is a halide atom and n is a constant determined as needed to balance the electronic charge.

Non-hydrolytic condensation reactions are also possible with these Sol-Gel materials. Building-up of the M-O-M network can also be achieved by condensation reactions between species with different ligands. Metal alkoxides and carboxylates (elimination of ester, equation 1), metal halides $MX_n$ and alkoxides (formation of alkylhalide—equation 2) or elimination of dialkylether (equation 3) as the source of the oxo ligand are examples.

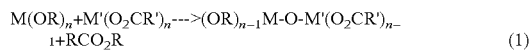

$$M(OR)_n + M'(O_2CR')_n \longrightarrow (OR)_{n-1}M\text{-}O\text{-}M'(O_2CR')_{n-1} + RCO_2R \quad (1)$$

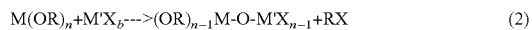

$$M(OR)_n + M'X_b \longrightarrow (OR)_{n-1}M\text{-}O\text{-}M'X_{n-1} + RX \quad (2)$$

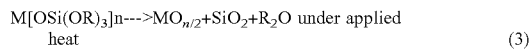

$$M[OSi(OR)_3]n \longrightarrow MO_{n/2} + SiO_2 + R_2O \text{ under applied heat} \quad (3)$$

Metal alkoxides can also be used as precursors of non-oxide materials. For instance, fluorinated alkoxides $M(OR_f)_n$ ($R_f$=$CH(CF_3)_2$, $C_6F_5$, ...) can decompose upon heating to give the base metal. Metal fluorides may result from these precursors depending on thermal treatment. The reactivity of the M-OR bond also provides ascention to phosphatessulfides or oxysulfides materials.

The hydrolysable metallic alkoxide precursors are selected so that they yield the desired metallic oxide material. The metallic oxide materials may have high k values (dielectric constant), baseline values, or low k values. The high k value materials deposited by the hydrolysis reactions have k values at least equal to about 10. Typical of such high k value materials are typically oxides, such as, for example, Ba—Sr—Ti—O (BST), Pb—Zr—Ti—O (PZT), and certain low atomic number metal oxides or mixed metal oxides, such as titanium oxide, hafnium oxide, zirconium oxide, aluminum oxide or hafnium-aluminum oxide. Silicon dioxide is generally considered the baseline material having a k value of around 4. Other baseline materials include boron phosphosilicate glass (BPSG) and phosphosilicate glass (PSG). Low k value materials (k less than about 3) can be derived from these materials by incorporating fluorine and/or carbon and/or porosity. Other low k value materials possible by this invention are hybrid inorganic-organic glasses that incorporate metal-organic bonds into the material. Representative of such hybrid glasses are organically modified silicate (Ormosil), organically modified ceramic (Ormocer), and silicon silsesquioxane materials.

The catalysts are acids or bases that are either soluble in supercritical carbon dioxide or are soluble when part of a Lewis acid-Lewis base complex. Suitable acids include organic acids, such as acetic acid, formic acid, and citric acid, as well as inorganic acids such as hydrofluoric acid (gaseous at the critical temperature of SCD), hydrochloric acid, nitric acid, sulfuric acid, and phosphoric acid. Many organic acids, and hydrofluoric acid, are soluble in supercritical carbon dioxide. Likewise, chlorine and bromine are gaseous at the critical temperature of SCD and form acids in contact with water). In contrast, many inorganic acids, especially strong inorganic acids, are not normally soluble in supercritical carbon dioxide. Such SCD-insoluble acids can form SCD-soluble complexes with SCD-soluble Lewis Bases. A particularly useful Lewis Base for forming these SCD-soluble complexes is tributyl phosphate. Tributyl phosphate is highly soluble in SCD and the inventors believe that the phosphate group can attach to acids, such as nitric acid or HCl, to increase the solubility of the acid by orders of magnitude. Suitable bases include ammonia, organic amines, pyridine or substituted pyridine, and fluoroamines. Strong inorganic bases, such as hydroxides, e.g., KOH or NaOH, can be used if they are solubilized by complexing with a Lewis acid that is soluble in supercritical carbon dioxide.

Generally, the hydrolysis reactions are limited by the low solubility of water in supercritical carbon dioxide. The scarcity of available water due to the low SCD-solubility of water is believed to be a major cause of the relatively slow reaction rates seen in earlier processes that did not use the current catalysts. For example, metal alkoxides are well-known to be moisture sensitive. Indeed, metal alkoxides will typically undergo hydrolysis slowly at room temperature and would be expected to rapidly hydrolyze at 100° C., even in the absence of a catalyst, if water was readily available.

In contrast to the previous art, in this method, the SCD-soluble acids, bases and/or acid/base-complexed catalysts interact with water molecules, so that the SCD-soluble catalysts work as carriers for water delivery in supercritical $CO_2$. This interaction greatly increases the availability of water for the hydrolysis reaction, which results in the desired increase in the hydrolysis reaction rate. For example, ammonia appears to have at least a one-to-one molecular interaction with water so that, on average, each dissolved ammonia molecule carries at least one water molecule.

The new acid or base catalyzed oxide deposition process in supercritical fluid is carried out in a high-pressure system with $CO_2$ pressure at least at the critical pressure of about 73 atm, typically greater than 80 atm. The concentrations of the precursors (alkoxides) and water dissolved in the supercritical fluid phase are usually high (several hundred tons or more) and consequently result in high deposition rates in relatively low temperatures. Preferably the reaction temperature is no more than about 150° C., more preferably no more than about 100° C.

When using the process of this invention, the deposition rate is generally fast, in the order of several hundred angstroms per minute. The oxide films formed by this method show good morphology and strong adhesion to silicon or other substrate surfaces. This method also allows deposition of oxides in fine structures of silicon wafers with high aspect ratios. The high diffusivity and low viscosity of supercritical carbon dioxide enables oxide deposition in small areas and fine structures with high aspect ratios. FIG.

1 shows SEM images of silicon dioxide films formed on a silicon wafer and also deposited in the small structures (100 nm wide and 500 nm deep trenches). As shown in FIG. 1, the silicon dioxide films are basically free of visible voids according to the SEM micrographs.

Although the oxide films produced by this method are typically free of large voids, the films are porous as indicated by the density of the deposited material. However, due to the lack of surface tension in SCD, the drying occurs without contractional forces from the liquid. As a result, the deposit material does not display "mud-cracking" typical of the drying of a normal fluid solvent. Generally, the oxide films formed by base catalyzed reactions are denser than the oxide films formed by acid catalyzed reactions. The densities of the oxide layers formed in by this inventive process are believed to be greater than 50% of the density of dense $SiO_2$ (2.2 $g/cm^3$).

Representative examples of acid or base catalyzed oxide formation reactions are described as follows:

$SiO_2$ Film Formation

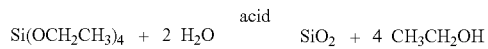

When acetic acid is used as the catalyst, a smooth silicon dioxide film with reasonable thickness can be formed in supercritical $CO_2$ at temperatures above 100° C. The deposition reaction actually starts at room temperature but produces good quality thick films at 100° C. In the absence of acetic acid, only uneven and thin silicon dioxide films (10-20 nm) can be formed. Addition of acetic acid makes the resulting silicon dioxide films uniform and thick. The thickness of the silicon dioxide films formed by reaction (1) can be up to 500 nm in the presence of 19 mole % to 95 mole % of acetic acid relative to TEOS. The acid catalytic reaction probably involves proton coordination to the oxygen atoms of TEOS molecule that facilitates the hydrolysis.

$SiO_2$ Film Formation
Alkoxide: tetraethyl orthosilicate (TEOS); Base catalyst: $NH_3$

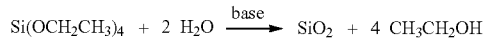

$HfO_2$ Deposition
Alkoxide: Hafnium tert-butoxide; Base catalyst: $NH_3$

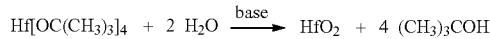

$Al_2O_3$ Deposition
Alkoxide: (a) Aluminum ethoxide and (b) Aluminum isopropoxide; Base catalyst: $NH_3$ (a) Aluminum ethoxide

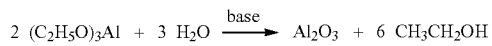

(b) Aluminum isopropoxide

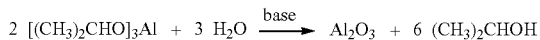

In compliance with the statute, the invention has been described in language more or less specific as to chemical, structural and methodical features. It is to be understood, however, that the invention is not limited to the specific features shown and described, since the means herein disclosed comprise preferred embodiments of putting the invention into effect. These embodiments are described in sufficient detail to enable those skilled in the art to practice the invention, and it is to be understood that other embodiments may be utilized and that changes may be made without departing from the spirit and scope of the present invention. The invention is, therefore, claimed in any of its forms or modifications within the proper scope of the appended claims appropriately interpreted in accordance with the doctrine of equivalents.

What is claimed is:

1. A method of increasing the solubility of a base in supercritical carbon dioxide, comprising:
    forming a complex of a Lewis acid and a base, wherein the Lewis acid is soluble in supercritical carbon dioxide, and the base is substantially insoluble in supercritical carbon dioxide; and
    dissolving the complex in superciitical carbon dioxide.

2. The method of claim 1, wherein forming a complex of a Lewis acid and a base comprises reacting the Lewis acid with a base selected from the group consisting of an organic amine, a substituted pyridine, a fluoroamine, potassium hydroxide, and sodium hydroxide.

3. A method for increasing the solubility of water in supercritical carbon dioxide, comprising:
    dissolving an acid or a base in supercritical carbon dioxide to form a solution, wherein the acid or the base is formulated to interact with water to solubilize the water in the supercritical carbon dioxide: and
    dissolving water in the solution.

4. The method of claim 3, wherein dissolving an acid or a base in supercritical carbon dioxide comprises dissolving an acid complexed with tributyl phosphate in the supercritical carbon dioxide.

5. The method of claim 3, wherein dissolving an acid or a base in supercritical carbon dioxide comprises dissolving an acid selected from the group consisting of acetic acid, formic acid, citric acid, hydrofluoric acid, hydrochloric acid, nitric acid, sulfuric acid, and phosphoric acid.

6. The method of claim 3, wherein dissolving an acid or a base in supercritical carbon dioxide comprises dissolving acetic acid in the supercritical carbon dioxide.

7. The method of claim 3, wherein dissolving an acid or a base in supercritical carbon dioxide comprises dissolving a base selected from the group consisting of ammonia, an organic amine, pyridine, a substituted pyridine, a fluoroamine, and a hydroxide.

8. The method of claim 3, wherein dissolving an acid or a base in supercritical carbon dioxide comprises dissolving ammonia in the supercritical carbon dioxide.

9. The method of claim 3, further comprising combining the solution with a hydrolyzable alkoxide.

10. The method of claim 3, wherein dissolving an acid or a base in supercritical carbon dioxide to form a solution comprises forming a complex comprising at least one of a Lewis acid and a Lewis base.

11. The method of claim 3, wherein dissolving an acid or a base in supercritical carbon dioxide to form a solution comprises dissolving at least one material in the supercritical carbon dioxide, wherein the at least one material alone is insoluble in supercritical carbon dioxide.

12. The method of claim 1, wherein forming a complex of a Lewis acid and a base comprises forming a complex of the base and the Lewis acid selected from the group consisting of acetic acid, formic acid, citric acid, and combinations thereof.

13. The method of claim 1, further comprising maintaining a temperature of the supercritical carbon dioxide at less than about 150° C.

14. A method comprising:
  combining supercritical carbon dioxide, a base that is soluble in the supercritical carbon dioxide, and an acid that is substantially insoluble in the supercritical carbon dioxide to form a supercritical carbon dioxide solution comprising a complex of the base and the acid, the complex soluble in the supercritical carbon dioxide;
  combining the supercritical carbon dioxide solution with a hydrolyzable alkoxide; and
  reacting the hydrolyzable alkoxide with water to form a solid material.

15. The method of claim 14, wherein reacting the hydrolyzable alkoxide with water to form a solid material comprises forming a solid material that is insoluble in the supercritical carbon dioxide solution.

16. The method of claim 14, wherein forming the solid material comprises forming a material having a dielectric constant of less than about 3.

17. The method of claim 14, wherein combining supercritical carbon dioxide, a base, and an acid comprises combining supercritical carbon dioxide, a Lewis base, and an acid.

18. The method of claim 14, further comprising dissolving water in the supercritical carbon dioxide solution.

19. The method of claim 18, wherein dissolving water in the supercritical carbon dioxide solution comprises dissolving water in the supercritical carbon dioxide solution at a higher concentration than a solubility limit of water in supercritical carbon dioxide alone.

20. The method of claim 14, further comprising maintaining a temperature of the supercritical carbon dioxide solution at less than about 150° C.

* * * * *

UNITED STATES PATENT AND TRADEMARK OFFICE
CERTIFICATE OF CORRECTION

PATENT NO.      : 9,676,944 B2  
APPLICATION NO. : 14/571525  
DATED           : June 13, 2017  
INVENTOR(S)     : Chien M. Wai, Hiroyuki Ohde and Stephen J. Kramer Page 1 of 1

It is certified that error appears in the above-identified patent and that said Letters Patent is hereby corrected as shown below:

In the Specification

| | | |
|---|---|---|
| Column 1, | Line 10, | change "Dec. 162014," to --issued Dec. 16, 2014,-- |
| Column 4, | Line 34, | change "structure M(OR)," to --structure $M(OR)_n$-- |
| Column 6, | Line 54, | change "hundred tons or" to --hundred torrs or-- |

Signed and Sealed this  
Twelfth Day of September, 2017

Joseph Matal  
*Performing the Functions and Duties of the*  
*Under Secretary of Commerce for Intellectual Property and*  
*Director of the United States Patent and Trademark Office*